(12) United States Patent
Chiba et al.

(10) Patent No.: US 8,344,103 B2
(45) Date of Patent: Jan. 1, 2013

(54) COMPATIBLE-MULTIPHASE ORGANIC SOLVENT SYSTEM

(75) Inventors: Kazuhiro Chiba, Musashono (JP); Yusuke Kono, Tokyo (JP)

(73) Assignee: Japan Science and Technology Agency, Saitama-ken (JP)

( * ) Notice: Subject to any disclaimer, the term of this patent is extended or adjusted under 35 U.S.C. 154(b) by 597 days.

(21) Appl. No.: 11/556,492

(22) Filed: Nov. 3, 2006

(65) Prior Publication Data
US 2007/0066799 A1   Mar. 22, 2007

Related U.S. Application Data

(62) Division of application No. 10/486,383, filed as application No. PCT/JP02/08501 on Aug. 23, 2002, now abandoned.

(30) Foreign Application Priority Data

Aug. 24, 2001   (JP) ................................. 2001-254109
Dec. 19, 2001   (JP) ................................. 2001-385493

(51) Int. Cl.
  *C07K 1/00*   (2006.01)
  *C07K 1/01*   (2006.01)
(52) U.S. Cl. ........................................ 530/333; 530/338
(58) Field of Classification Search ........................ None
    See application file for complete search history.

(56) References Cited

OTHER PUBLICATIONS

Tamiaki, 1998, Peptide Science, M. Kando (Ed.), 125-128.*
Bergbreiter, 2000, JACS, 122, 9058-9064.*
Tamiaki, 1999, Peptide Science, 35, pp. 733-738.*
Vani, Coexistence Curve and Critical Point Wetting in the Binary Liquid Mixture Cyclohexane + Acetonitrile, Dec. 1982, Physics Letter, vol. 99A, No. 9.
Theon, The Dilelectric Constant Anomaly of Nitroethane-Cyclohexane near the Critical Solution Point, Dec. 1981, Physics Letter, vol. 87A, No. 1,2.
Bonn, Wetting and prewetting in a binary fluid mixture, 1994, J.Phys: Condens. Matter 6, A389-A394.
Chiba, Electrochemical synthesis of chroman and euglobal skeletons via cycloaddition reaction of o-quinone methides and alkenes, 1996, J. Chem. Soc.. Perkin Trans 1.
Tamiaki, A Novel Protecting Group for Constructing Combinatorial Peptide Libraries, 2001, The Chemical Society of Japan, Bull. Chem. Soc. Jpn.,74, pp. 733-738.

* cited by examiner

*Primary Examiner* — Karlheinz R Skowronek
*Assistant Examiner* — Satyanarayana R Gudibande
(74) *Attorney, Agent, or Firm* — Hahn & Voight PLLC; Roger C. Hahn

(57) ABSTRACT

A solvent system which comprises two or more single organic solvents or two or more mixed organic solvents, characterized in that the state of the solvent system can be reversibly changed, with changing temperature conditions, from one state which is a homogeneously compatibilized mixed solvent system in which the two or more single or more mixed organic solvents constituting the solvent system have been homogeneously compatibilized and mixed to the other state which is a separated solvent system made up of two or more separated phases respectively consisting mainly of the two or more single or mixed organic solvents constituting solvent system, and that when the solvent system is the homogeneously mixed solvent system, a chemical component which is soluble in only one of the single or mixed organic solvents can be evenly dissolved in the system; and a process for producing a compound with the solvent system.

11 Claims, 5 Drawing Sheets mixing ratio (volume)

COMPATIBLE-MULTIPHASE ORGANIC SOLVENT SYSTEM

CROSS REFERENCE TO RELATED APPLICATIONS

This application is a divisional application of Ser. No. 10/486,383, having a filing or §371(e) date of Feb. 10, 2004, which is a national stage application of PCT/JP02/08501 dated Aug. 23, 2002, claming foreign priority to JP 2001-254109 dated Aug. 24, 2001, and JP 2001-385493 dated Dec. 19, 2001.

FIELD OF THE INVENTION

The present invention basically relates to a solvent system characterising that the controlling of the reaction is easy and the recovery of the reaction product is easy, further relates to a method for preparation of chemical compound utilizing said reaction solvent system.

Further specifically, the present invention is the solvent system comprising two or more single organic solvents or two or more mixed organic solvents, and this solvent system is characterized as follows. That is, said solvent system can change the state reversibly by changing temperature condition from one state which is the homogeneously compatibilized mixed solvent system in which two or more single organic solvents or two or more mixed organic solvents constituting the solvent system are homogeneously compatibilized and mixed to another one state which is the separated solvent system in which the solvent system is separated into two or more phases consisting mainly of the two or more single organic solvents or mixed organic solvents constituting the solvent system, and can dissolve the chemical component which is soluble in only one single organic solvent or mixed organic solvent homogeneously. Still more, the present invention is a method for preparation of compound which makes easy the controlling of reaction and the separation and the recovery of the product comprising, progressing the compound reaction in the homogeneously compatibilized mixed solvent system in which two or more single organic solvents or mixed organic solvents constituting the solvent system are homogeneously compatibilized, then stopping substantially said reaction by separating it into two or more phases consisting mainly of the two or more single organic solvents or mixed organic solvents, recovering the generated product in one phase composing single organic solvents or mixed organic solvents as the main component or recovering as the deposit.

Furthermore, for example, in the system which uses electrolyte, the present invention relates to the solvent system which can easily change the state reversibly from the state of the homogeneously compatibilized mixed solvent system dissolving the electrolyte to the state of separated solvent which makes possible to separate the electrolyte by dissolving the electrolyte in one separated phase consisting mainly of the two or more single organic solvents or mixed organic solvents, the reactive solvent system and the method for preparation of compound utilizing said reactive solvent system, still further the present invention relates to the method for synthesis of polymer compound such as peptide making possible to utilize above mentioned reactive solvent system, by finding out a compound residue having the function to dissolve the compound having a bonding part of amino acid unit from which the formation of peptide in conventional solid-phase peptide synthesis is initiated, a function to load peptide chain extended by bonding the amino acid units in order and a bonding part of amino acid unit before the starting of synthesis of the peptide and the compound to which synthesizing peptide chain is bonded into one solvent or into mixed solvent system, by other words, by transferring the compound to be used in the reaction to the compound which can utilize the compativility-multiphase organic solvent system.

BACKGROUND OF THE INVENTION

In chemical reaction, if it becomes possible to separate easily the aimed product from catalyst, additives for reaction or by-products, not only the numbers of necessary operations for separation can be reduced largely, but also the generation of wastes harmful to the environment can be effectively reduced by decreasing the numbers of agents used in the process. While, as the methods to separate the product easily in investigation stage, following methods were already proposed.

1. Solid-phase synthesis characterizing that the series reactions of molecules locating on the surface of solid dispersed in solvent with molecules dissolved in the solvent are carried out on the surface of solid in the state that the solid is dispersed in solvent.

2. Fluorine compativility-two-phases reaction systems characterized that fluorinated alkanes and the ordinary low polar organic solvent are combined.

3. Reaction system which uses a phase-transfer catalyst in double phases consisting of water and organic solvent.

4. Reaction system in the combination of two or more kinds of organic solvents which control the chemical reactivity of polymer or compound whose ligand is polymer and the refining by separation by changing dissolving ability of polymer carrier which is dissolved or dispersed in solvent, by changing the state of phase separation.

In these reaction systems, the method 2, each components consisting of the solvent are compatible by heating. However, the usable solvent is limited to the low polar solvent which has relatively high affinity with fluorinated solvent of low polar. Further, this method has problems, that is, expensive fluorinated solvent is necessary, the substance to be dissolved is necessary to be fluorinated because it is dissolved in fluorinated solvent, and in the case of reaction dissolving an organic or an inorganic salt, there is a difficulty to handle a polor substance such as biomolecule, because high permittivity solvent does not have this characteristic.

Further, the method 3 can be said as the reaction system which combines high permittivity or high polar solvent with low permittivity or low polar solvent. Although these solvents forms two-phases structure according to the difference of the physical property, the solvent which forms reversibly homogeneous compatible mixed solvent by simplified change of outer condition is not obtained yet. Further, the reaction is limited at the interface of separated two layers, and the reactivity can not be said to be high.

As disclosed in the method 4, when polymer is used as a solute or as an agent, the separation of low molecule component and polymer component accompanying to the phase separation of the solvent can be easily controlled. In the meanwhile, in many chemical reactions, the reaction between low molecule components is carried out. However, in the chemical reaction which uses plural numbers of low molecule substances, the separation of the aimed product from not necessary substances by utilizing strictly the difference of solubility between these low molecule substances in actual level was considered to be difficult. The reason why can be illustrated as follows. That is, when two-phase separation state is formed by combining two or more organic solvents, the components in upper layer solvent and in lower layer solvent are not composed by single component but main component solvent of another layer is mixed.

Therefore, the subject of this invention is to construct the reaction system which solve the problem of controlling the reaction and the problem of separation and refining of the reacted product. In earnest study to solve these problems, the inventors of the present invention have found that the specific non polar organic solvent and polar organic solvent have different solubility to the chemical component and can transfer reversibly and easily to two solvent states, that is, the homogeneous compatibilized mixed solvent state and the separated solvent state in which the phase is separated by only changing the temperature condition, further, can separate single or plural low molecule solute components whose physical properties are different spatially and almost completely, still further, the substantial reaction condition is only satisfied in homogeneous compatibilized mixed solvent state, thus dissolved above mentioned problems.

Above mentioned non polar organic solvent and polar organic solvent are respectively single organic solvent composed of one organic solvent or mixed organic solvent which mixes two or more solvents belonging to each organic solvent by adequate mixing ratio.

At the dissolving of said problem, for example, the polar solvent which dissolves ordinary electrolyte does not form the homogeneous compatibilized mixed solvent state with non polar organic solvent by simple condition, and especially it is difficult to make it reversible. However, in the solvent system which is found out by the inventors of the present invention, one solvent can dissolve electrolyte, and the homogeneous compatibilized mixed solvent state dissolving electrolyte—the separable state by dissolving electrolyte only in single organic solvent mainly composed of one organic solvent which is phase separated or mixed organic solvent can be accomplished reversibly only by controlling the temperature. The discovery of this phenomenon is an unexpected one, and said solvent system is extremely useful for the designing and construction of various reaction system in the future, because ionic substance is frequently used in the reaction system and the separation of ionic substance after reaction is difficult. Further, this solvent system can construct the functional system which control not only reaction process but also refining process, compatibility—phase separation, for example, the system which flows an electric current at the critical temperature, and is hopeful as the new functional material.

Further, the inventors of the present invention are aimed to use said solvent system practically and have synthesized the compound which is utilized so as the practical use of the solvent system to be possible, for example, have designed the compound having a bonding part of amino acid unit from which the formation of peptide in the method for peptide synthesis is initiated with a residue which make the utilization of the solvent system possible such as the compound represented by following general formula A, and have constructed the reaction system utilizing the solvent system positively.

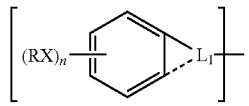

General formula A

In general formula A, $L_1$ is hydroxyl group which bonds with amino acid, a single bond which bonds with thiol group, amino group or carbonyl group, an atomic group which bonds with said hydroxyl group, thiol group, amino group or carbonyl group or an atomic group which forms fused aromatic ring of two rings bonding with dotted line, wherein the dotted line is an atomic group which forms said fused aromatic ring by bonding with H or $L_1$, X is O, S, ester group, sulfide group or imino group, R is hydro carbon group of carbon number 10 or more which can contain O, S or N having a possibility to improve the solubility to cycloalkane solvents as a bonding atom, n is a integer from 1 to 5, further in the case when said hydro carbon group of carbon number 10 or more is to improve the solubility to cycloalkane solvents, R possesses a side chain with functional group which bonds with the amino group and/or substituent.

From the technical view point, the residue of the compound represented by general formula A is called as carrier in the present invention.

This peptide synthesis reactions can be applied to the synthesis of oligomers or polymers such as protein, DNA, RNA or polysaccharides.

DISCLOSURE OF THE INVENTION

A. The $1^{st}$ one of the present invention is a solvent system comprising, two or more single organic solvent or mixed organic solvent, and said solvent system can change the state reversibly by changing temperature condition from one state which is a homogeneously compatibilized mixed solvent system in which two or more single organic solvents or mixed organic solvents constituting the solvent system are homogeneously compatibilized and mixed to another one state which is a separated solvent system in which the solvent system is separated into two or more phases consisting mainly of the two or more single organic solvents or mixed organic solvents constituting the solvent system, and can dissolve the chemical component which is soluble in only one single organic solvent or mixed organic solvent homogeneously.

In the meanwhile, the wording of "is soluble in only one single organic solvent or mixed organic solvent" does not mean that can not be dissolved in other single organic solvent or mixed organic solvent at all, but the concept including the case that the greater part of added chemical component is dissolved in one single organic solvent or mixed organic solvent, and several % of added chemical component is dissolved in another single organic solvent or mixed organic solvent.

B. Desirably, the $1^{st}$ on of the present invention is the solvent system of A, wherein the chemical component takes part in the reaction, and a phase whose main component is at least one organic solvent or organic solvents constructing the solvent system dissolves at least one component of the chemical components which take part in the reaction, and in the state of separated solvent does not satisfy the condition which progress the substantial chemical reaction, and only in the state of homogeneous compatibilized mixed solvent system satisfies the condition which progress the substantial chemical reaction.

C. More desirably, the $1^{st}$ on of the present invention is the solvent system of A or B, wherein one single organic solvent or mixed organic solvent is composed of cycloalkanes and another single organic solvent or mixed organic solvent is composed of at least one selected group consisting of nitroalkane, nitrile, alcohol, halogenated alkyl, amide and sulfoxide.

D. Further desirably, the $1^{st}$ on of the present invention is the solvent system of C, wherein carbon number of alkyl group of nitro alkane is 1, 2 or 3, carbon number of alkyl group of nitrile is 1, 2 or 3, amide is N-dialkyl or N-monoalkyl amide, the total carbon number of alkyl group and formyl group or acyl group is 6 or less, carbon number of alcohol is 8 or less, carbon number of alkyl group of sulfoxide is 1, 2 or 3 and carbon number of alkyl group of halogenated alkyl is 6 or less.

E. The $2^{nd}$ one of the present invention is the method for preparation of the compound comprising, using the solvent system of two or more single organic solvent or mixed organic solvent, and said solvent system can change the state reversibly by changing temperature condition from one state which is a homogeneously compatibilized mixed solvent system in which two or more single organic solvents or mixed organic solvents constituting the solvent system are homogeneously compatibilized and mixed to another one state which is a separated solvent system in which the solvent system is separated into two or more phases consisting mainly of the two or more single organic solvents or mixed organic solvents constituting the solvent system, and can dissolve the chemical component which is soluble in only one single organic solvent or mixed organic solvent homogeneously, using a chemical component which takes part in the reaction as chemical component, after said chemical component is added, the reaction is progressed under the temperature condition realizing the state of homogeneous compatibilized mixed solvent system which satisfy the condition of chemical reaction, then the condition is changed to the temperature by which two or more single organic solvent or mixed organic solvent is separated into two or more phases consisting mainly of the two or more single organic solvents or mixed organic solvents, recovering by separating the generated product in one phase composing single organic solvents or mixed organic solvents as the main component as a deposit.

F. Desirably, the $2^{nd}$ one of the present invention is the method for preparation of the compound of E, wherein one single organic solvent or mixed organic solvent is composed of cycloalkanes and another single organic solvent or mixed organic solvent is composed of at least one selected group consisting of nitroalkane, nitrile, alcohol, halogenated alkyl, amide and sulfoxide.

G. More desirably, the $2^{nd}$ one of the present invention is the method for preparation of the compound of F, wherein carbon number of alkyl group of nitro alkane is 1, 2 or 3, carbon number of alkyl group of nitrile is 1, 2 or 3, amide is N-dialkyl or N-monoalkyl amide, the total carbon number of alkyl group and formyl group or acyl group is 6 or less, carbon number of alcohol is 8 or less, carbon number of alkyl group of sulfoxide is 1, 2 or 3 and carbon number of alkyl group of halogenated alkyl is 6 or less.

H. The $3^{rd}$ one of the present invention is the method for preparation of the compound of E, F and G, wherein electrolyte is used as the chemical component which takes part in the reaction, and the reaction is progressed by electrolysis.

I. The $4^{th}$ one of the present invention is the method for preparation of the compound of above mentioned items, wherein the reaction is progressed by irradiating the light of ultra violet—visible light.

J. The $5^{th}$ one of the present invention is the method for preparation of peptide utilising the solvent system of A and specifically mentioned as follow. That is, the $5^{th}$ one of the present invention is the method for preparation of peptide by liquid phase synthesis comprising,
using the combination with carrier induced from the compound possible to improve the solubility to one solvent composing solvent system which can control said condition or to the mixed solvent A as the residue to introduce amino acid residue to the carboxy end of peptide to be synthesized,
the solubility of the compound whose peptide chain is extended by introducing amino acid gradually to peptide starting compound bonded with amino acid residue carrier of carboxy end of peptide to be synthesised or to said peptide starting compound to said solvent or mixed solvent A is improved,
using the solvent which dissolves various amino acids used for the extension of said peptide chain preferentially at the lower temperature than the temperature to form mentioned compatibilized condition and at the higher temperature than the temperature to form mentioned compatibilized condition forming a solvent in compatibilized condition and dissolving the peptide starting compound as another solvent to be combined with said solvent or mixed solvent A or mixed solvent B,
substituting above mentioned B which dissolves protective amino acid bonding a protective group at various a position amino group with the solvent which dissolves amino acid synthesises gradually designed peptide in the condition of phase separation, then heating to the temperature showing compatibilized state after substitution.

K. Desirably, the $5^{th}$ one of the present invention is the method for preparation of peptide by liquid phase synthesis of J, wherein the organic solvent composing one solvent or mixed solvent is composed by cycloalkane compounds, and organic solvent composing another solvent or mixed solvent B to be combined with the organic solvent composing said solvent or mixed solvent A is at least one selected from the group consisting of nitroalkane, nitrile, alcohol, halogenated alkyl, amide and sulfoxide.

L. More desirably, the $5^{th}$ one of the present invention is the method for preparation of peptide by liquid phase synthesis of J, wherein carbon number of alkyl group of nitro alkane is 1, 2 or 3, carbon number of alkyl group of nitrile is 1, 2 or 3, amide is N-dialkyl or N-monoalkyl amide, the total carbon number of alkyl group and formyl group or acyl group is 6 or less, carbon number of alcohol is 8 or less, carbon number of alkyl group of sulfoxide is 1, 2 or 3 and carbon number of alkyl group of halogenated alkyl is 6 or less.

M. The $5^{th}$ one of the present invention is the method for preparation of peptide by liquid phase synthesis of J, K and L, wherein the carrier which forms the peptide starting compound is the residue from aromatic hydrocarbon ring represented by general formula A or fundamental skeletal compound having 10 or more carbons having a functional group which can bond with amino acid with cycloalkanephilic solvent part.

N. Desirably, the $5^{th}$ one of the present invention is the method for preparation of peptide by liquid phase synthesis of M, wherein the compound represented by general formula A is the compound selected from the group of represented by general formulae B.

General formulae B

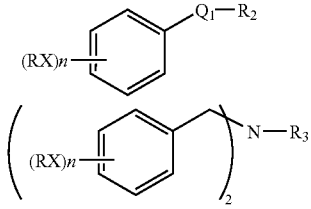

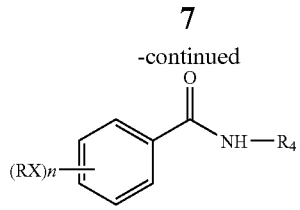

In above mentioned general formulae B, X, R and n are same as to that of general formula A. Q is a single bond or hydro carbon group, $R_2$ is hydroxyl group, thiol group, amino group or carbonyl group which bonds with amino acid, $R_3$ and $R_4$ is a group represented by general formula C,

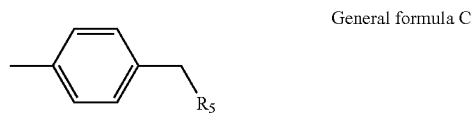

General formula C $R_5$ is hydroxyl group, thiol group, amino group or carbonyl group which bonds with amino acid.

BRIEF ILLUSTRATION OF THE DRAWING

FIG. 1 shows the state of solvent A' in which starting material is dissolved and solvent A" in which catalyst and reaction additive agents are dissolved are respectively separated to single organic solvent or mixed organic solvent. B illustrates the process B which progresses the reaction by adjusting the temperature condition to the state of homogeneous compatibilized mixed solvent system. C illustrates the separated solvent system which is separated reversibly to each solvent phase whose main component are solvents composing the solvent system, for example, separated to the solution phase C' which dissolves the product and the solution phase C" in which the catalyst and the reaction additive agent are dissolved. Namely FIG. 1 illustrates the method to separate the product and to recycle the catalyst and the reaction additive agent according to the theory of the solvent system of the present invention.

Figure 5:
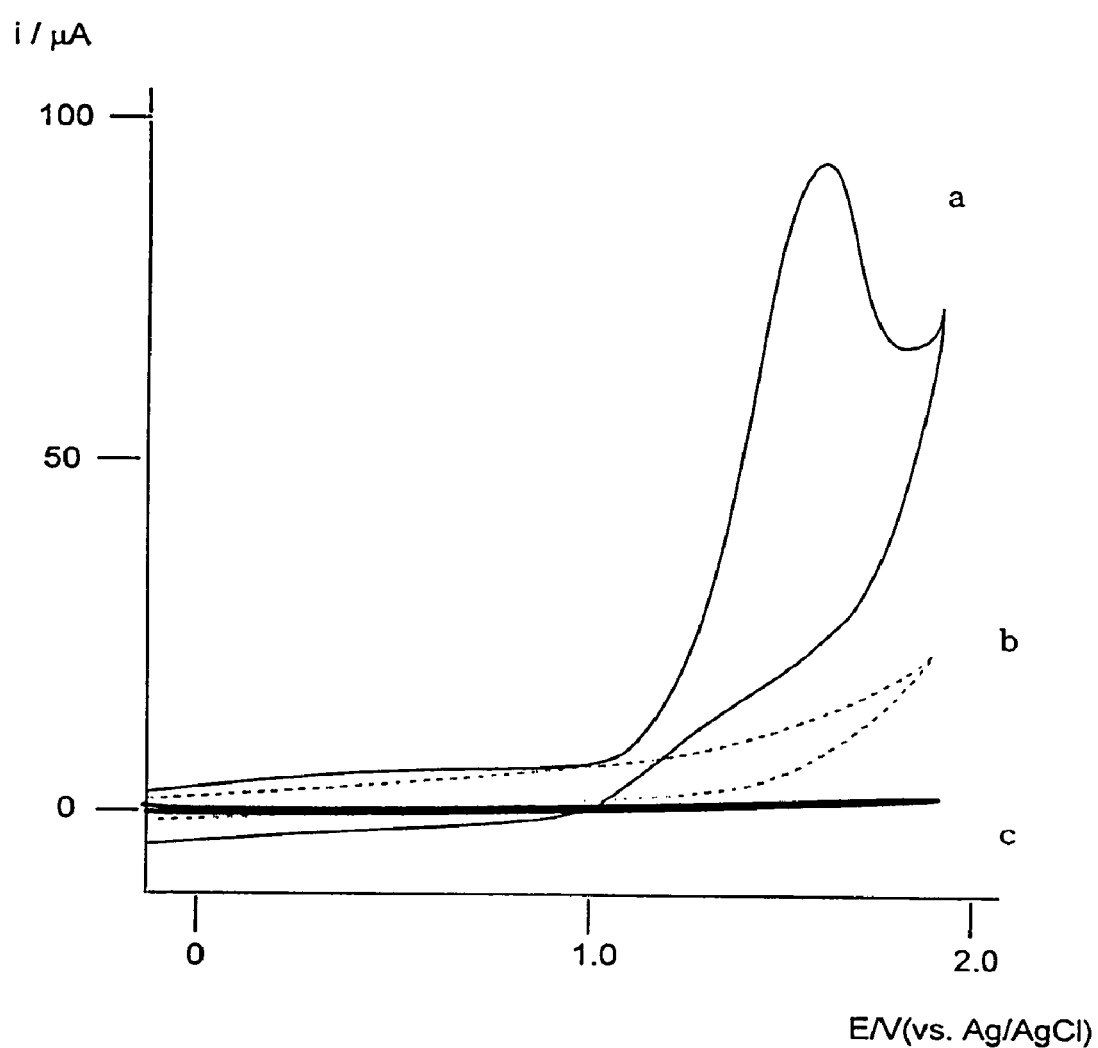

FIG. 5 shows the measuring results of state change of homogeneous compatibilized mixed solvent system—separated solvent system and selective oxidation reaction using solvent system containing electrolyte and oxidisable organic compound measured by following method. That is, a glassy carbon electrode (working electrode), a platinum cathode and silver-silver chloride electrode are inserted and cycled from −0.2 to 2.0 volt and potential is changed by 100 mv/second, and corresponding electric current is measured a is the case when homogeneous compatibilized mixed solvent system is formed by heating to 55° C., b is the case of nitroalkane phase of 20° C., and c is the case of cycloalkane phase of 20° C.

DESCRIPTION OF THE PREFERRED EMBODIMENT

The present invention will be illustrated in more detail. A. The solvent system of the present invention is composed of two or more kind of single organic solvent or mixed organic solvent which can reversibly form the state of homogeneous compatibilized mixed solvent system and the state of separated solvent system which is separated to plural phases by small temperature change.

The combination of single organic solvent or mixed organic solvent which has this characteristic is the base of the solvent system of the present invention.

1. One single organic solvent or mixed organic solvent is basically a low polar solvent, and as the compounds which compose said solvent, alkane, cycloalkane, alkene, alkyne or aromatic compound, desirably cycloalkane compound, more desirably cyclohexane can be mentioned. From the fact that the transformation of chair conformation—boat conformation isomer of cyclohexane can be carried out by comparative mild condition in connection with other solvent, it can be guessed that the solvent system of the present invention is realised. By this guessed characteristic, in said two phases solvent system, it is possible to consider to form the state that the majority part of solutes are distributed almost completely to either one phase. Further, since the melting point of cyclohexane is 6.5° C. and is relatively high, cyclohexane has a merit which can separate the reactive product by solidification. Therefore, from this view point, cyclohexane can be said as a desirable solvent.

2. As the single organic solvent or mixed organic solvent to be combined with above 1, basically the high polar organic solvent can be mentioned. Desirably, the solute having high polar which dissolves selectively the compound, for example, inorganic salts, organic salts, inorganic base, inorganic acid, organic base, organic acid, Lewis acid, Lewis base, amphoteric ion substance, ionic photo sensitizer (methylene blue), supporting electrolyte, organic metal compound, polar organic molecule such as alcohol, phenol, aromatic compound, carboxylic acid, amine, aldehyde, ketone, ether, amide, nitro compound, halogenide, thiol, sulfone, sulfoxide, isonitrile, acid anhydride or esters, water, polar polymer, amino acid, peptide, protein and derivatives thereof, nucleic acid and derivatives thereof, saccharide and derivatives thereof, lipid and derivatives thereof can be mentioned. As the more desirable solvent, nitroalkane, nitrile, alcohol, halogenated alkyl, amide and sulfoxide can be mentioned.

Because said solvent system is necessary to be used in various reactions, the solvent system is necessary to dissolve solute, catalyst, carrier and additives to be used in the reaction in the state of homogeneous compatibilized mixed solvent system, and is necessarily selected from this view point.

For example, when cyclohexane is used as the solvent to dissolve the product, following advantage can be mentioned. That is, the product can be separated as solid by cooling the solution to 0° C., and the product which is separated as the solid is heated to vaporize and remove the coexisting cyclohexane, thus the product can be refined easily.

3. For the establishment of above mentioned method for preparation of peptide by liquid phase synthesis, it is important to select the compound which improve the solubility in one single organic solvent or mixed organic solvent in the state of separated solvent system, while does not dissolved in another single organic solvent or mixed organic solvent to be combined with said one single organic solvent or mixed organic solvent as the peptide starting compound. As the compound having said physical property, the residue represented by general formula A and the residue from the fundamental skeletal compound of hydrocarbon group having 10 or more carbons.

4. As the amino acid used in the method for preparation of peptide by liquid phase synthesis, protective amino acid used in the conventional method for preparation of solid phase peptide, for example, Fmoc (9-fluorenylmethoxycarbonyl)-amino acid, Boc (t-butoxycarbonyl) amino acid or Cbz (bezyloxycarbonyl)-amino acid can be used.

5. The outline of extending process of peptide chain consisting of soluble carrier [SC]-valine(Val)-glycine-Fmoc (SC)-Val-Gly-Fmoc) using soluble carrier [SC] is shown as follows.

Example 1

Under the condition of 10° C., 1 atmospheric pressure, to 10 mL of cyclohexane contained in a reactive container (glass), 50 mL of nitroalkane was added. The mixture of nitromethane and nitroethane was used as nitroalkane. As the mixture, the mixtures of following mixing ratio were prepared. 10:0 (50 mL:0 mL), 9:1 (45 mL:5 mL), 8:1 (40 mL:10 mL), 7:3 (35 mL:15 mL), 6:4 (30 mL:20 mL), 5:5 (25 mL:25 mL), 4:6 (20 mL; 30 mL), 3:7 (15 mL:35 mL), 2:8 (10 mL:40 mL), 1:9 (5 mL:45 mL) and 0:10 (0 mL:50 mL).

Among these 11 kinds of organic solvent mixture, the mixtures of mixing ratio of nitromethane:nitroethane is from 10:0 to 3:7 were separated to 2 phases (upper layer whose main component is cyclohexane and lower layer whose main component is nitroalkane) at 10° C.

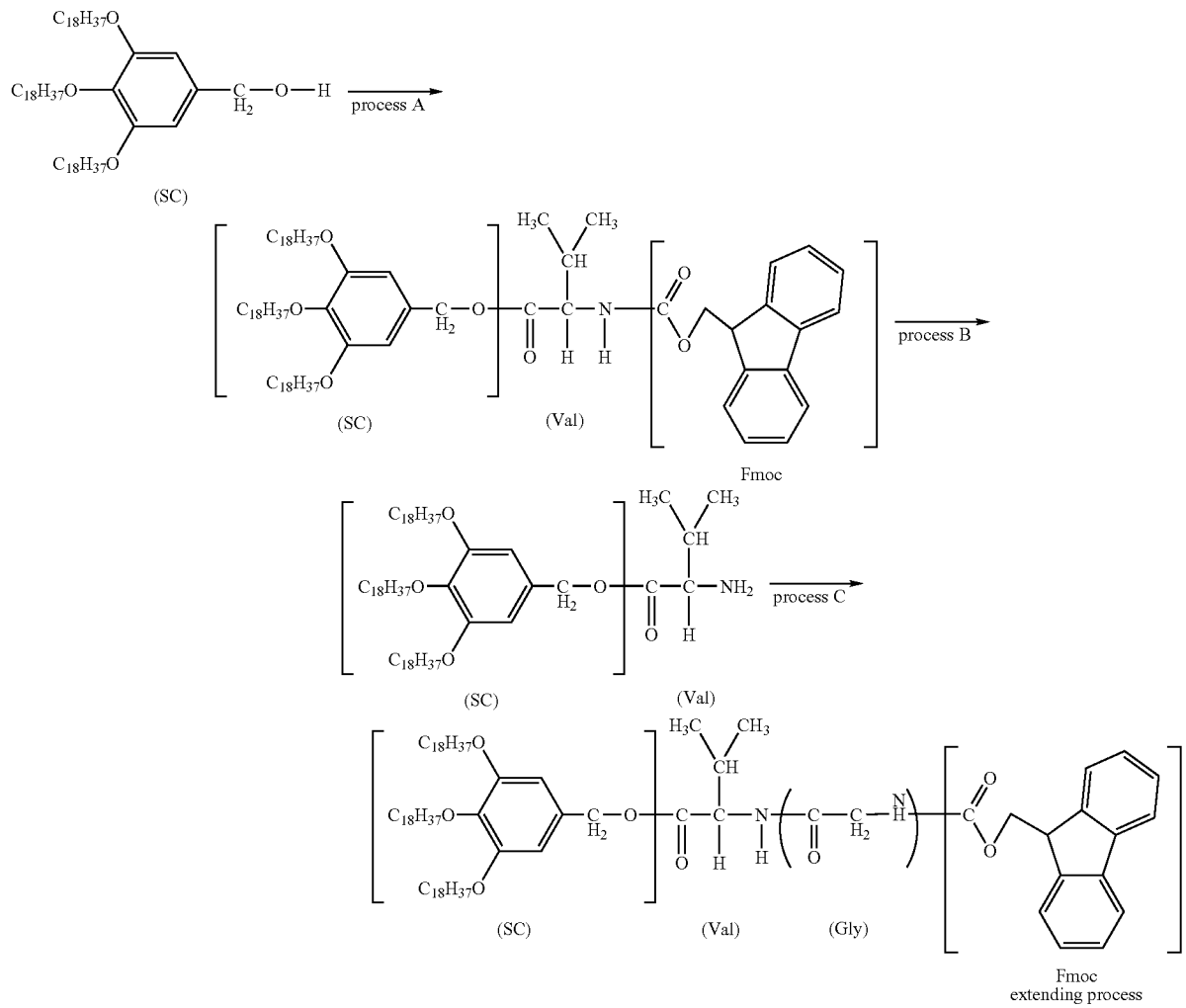

EXAMPLES

The present invention is illustrated according to the Examples, however, not intending to limit the scope of claims of the present invention.

First of all, the specified example of the solvent system is illustrated.

Figure 1:
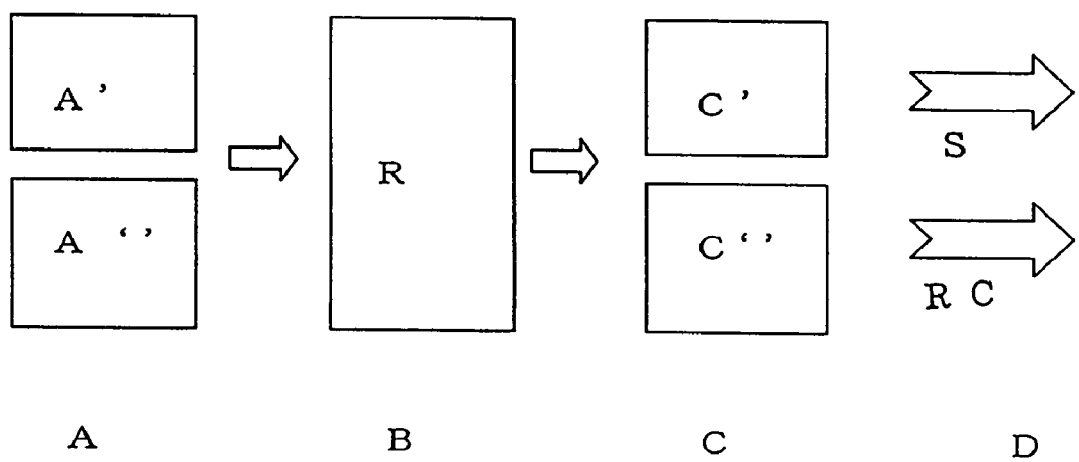
Figure 2:
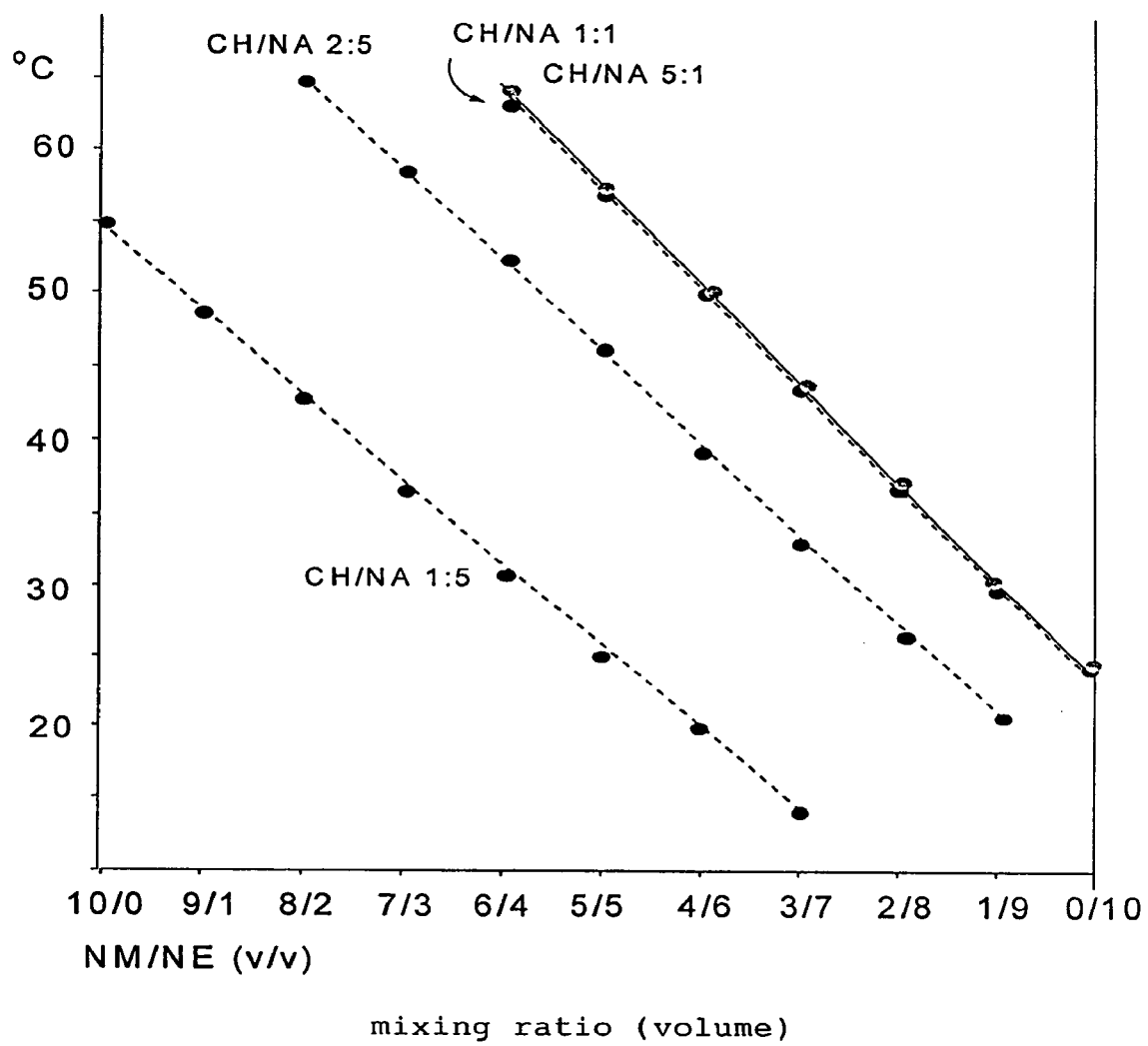
FIG. 2 shows the correlation between mixing ratio, temperature and state change of compatibility of cyclohexane CH: homogeneous compatibilized mixed solvent system of nitroalkane [nitromethane NM, nitroethane NE] solvent system—separated solvent system.

When the temperature of these solvents were elevated gradually, these solvents became complete homogeneous compatibilized mixed solvents by elevating the temperature over than the temperature shown in the graph of FIG. 2. These homogeneous compatibilized mixed solvent systems could maintain the state of homogeneous solution without performing physical operation such as stirring from outside, as long as keeping the temperature higher than the homogenized temperature. And, when the solvents were cooled down lower than the homogenized temperature, these solvents separated to two phases (separated solvent system) immediately. The state change phenomenon of homogeneous compatibilized mixed solvent system—separated solvent system was possible repeatably and reversibly to be performed along with heating or cooling process. Further, the solvents of nitromethane:nitroethane ratio is from 2:8 to 0:10 became homogeneous solvent at the temperature of 10° C. and separated to two phases by cooling down And by heating these solvents became homogeneous compatibilized mixed solvent again, that is, regarding these solvents the state change phenomenon of homogeneous compatibilized mixed solvent system—separated solvent system could be repeated reversibly.

Example 2

When cyclohexane:nitroalkane (nitroalkane is nitromethane or nitroethane or mixture thereof) ratio in Example 1 was changed, the temperature which shows the state change of homogeneous compatibilized mixed solvent system—separated solvent system was changed. As shown in FIG. 2, in the case of cyclohexane:nitroalkane ratio is 2:5 (cyclohexane 20 mL:nitroalkane 50 mL), when the constitution of nitroalkane (mixture of nitromethane:nitroethane) was changed, the temperature showing the state of homogeneous compatibilized mixed solvent system was changed same as to Example 1, however this temperature is higher than that of the case of cyclohexane:nitroalkane ratio is 1:5 by about 25° C. Further in the case of cyclohexane:nitroalkane ratio is 1:1 (cyclohexane 30 mL:nitroalkane 30 mL), the temperature showing the state of homogeneous compatibilized mixed solvent system became more higher. However, when the ratio of cyclohexane was increased than the case of cyclohexane:nitroalkane ratio is 1:1, the temperature showing the state change of homogeneous compatibilized mixed solvent system—separated solvent system was not changed more. From this fact, it became clear that this solvent mixture can form the state of homogeneous compatibilized mixed solvent system—separated solvent system by changing the ratio of cyclohexane, nitromethane and nitroethane.

This tendency was observed in the mixed organic solvent systems, that is, cydohexane-acetonitrile, cyclohexane-acetonitrile-voluntary organic solvent (for example, propionitrile) or cyclohexane-nitroalkane-voluntary organic solvent (for example, dimethylformamide).

Example 3

Figure 3:
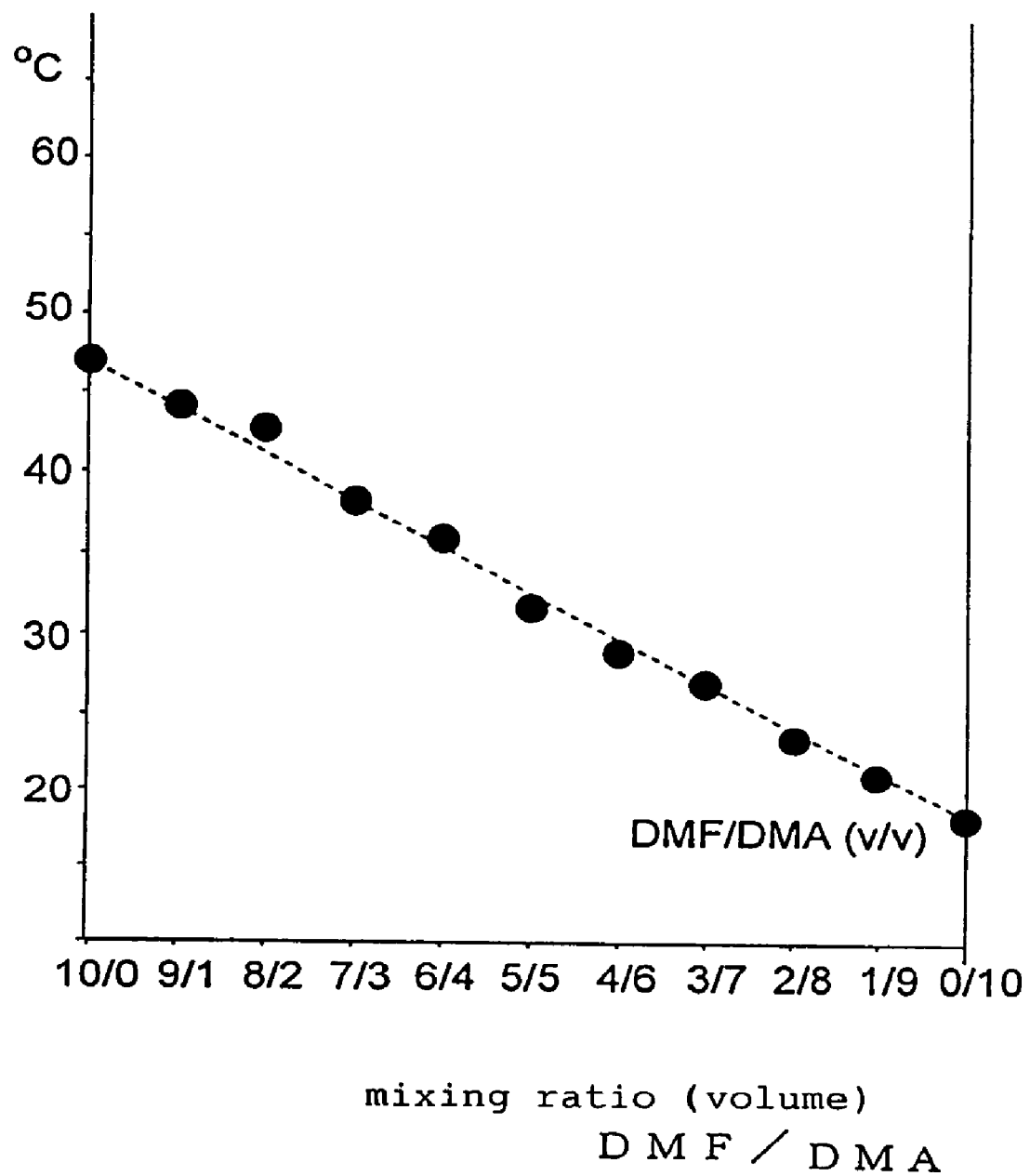
FIG. 3 shows the temperature characteristic of state change of cyclohexane—dimethyl formamide (DMF)—dimethylacetoamide (DMA) mixed solvent system to homogeneous compatibilized mixed solvent system.

The temperature characteristic of the state change of cyclohexane—dimethylformamide(DMF)—dimethylacetoamide (DMA) mixed solvent system to homogeneous compatibilized mixed solvent system. FIG. 3.

Under the condition of 10° C., 1 atmospheric pressure, to 50 mL of cyclohexane contained in a reactive container (glass), 50 mL of combined solvent system of dimethylformamide (DMF) and dimethylacetoamide (DMA) which are amide organic solvent was added. As the amide organic solvents, the mixture of DMF and DMA whose mixing ratio were changed as follows were prepared. 10:0 (50 mL:0 mL), 9:1 (45 mL:5 mL), 8:1 (40 mL:10 mL), 7:3 (35 mL:15 mL), 6:4 (30 mL:20 mL), 5:5 (25 mL:25 mL), 4:6 (20 mL; 30 mL), 3:7 (15 mL:35 mL), 2:8 (10 mL:40 mL), 1:9 (5 mL:45 mL) and 0:10 (0 mL:50 mL) All these 11 kinds of organic solvents mixture were separated to 2 phases (upper layer whose main component is cyclohexane and lower layer whose main component is amide organic solvents) at 10° C. When the temperature of these solvents were elevated gradually, these solvents became complete homogeneous compatibilized mixed solvents by elevating the temperature over than the temperature shown in the graph. These homogeneous compatibilized mixed solvent systems could maintain the state of homogeneous solution without performing physical operation such as stirring from outside, as long as keeping the temperature higher than the homogenized temperature. And, when the solvents were cooled down lower than the homogenized temperature, these solvents were separated to two phases (separated solvent system) immediately. The state change phenomenon of homogeneous compatibilized mixed solvent system—separated solvent system was possible repeatably and reversibly to be performed along with the heating or cooling process.

Example 4

Figure 4:
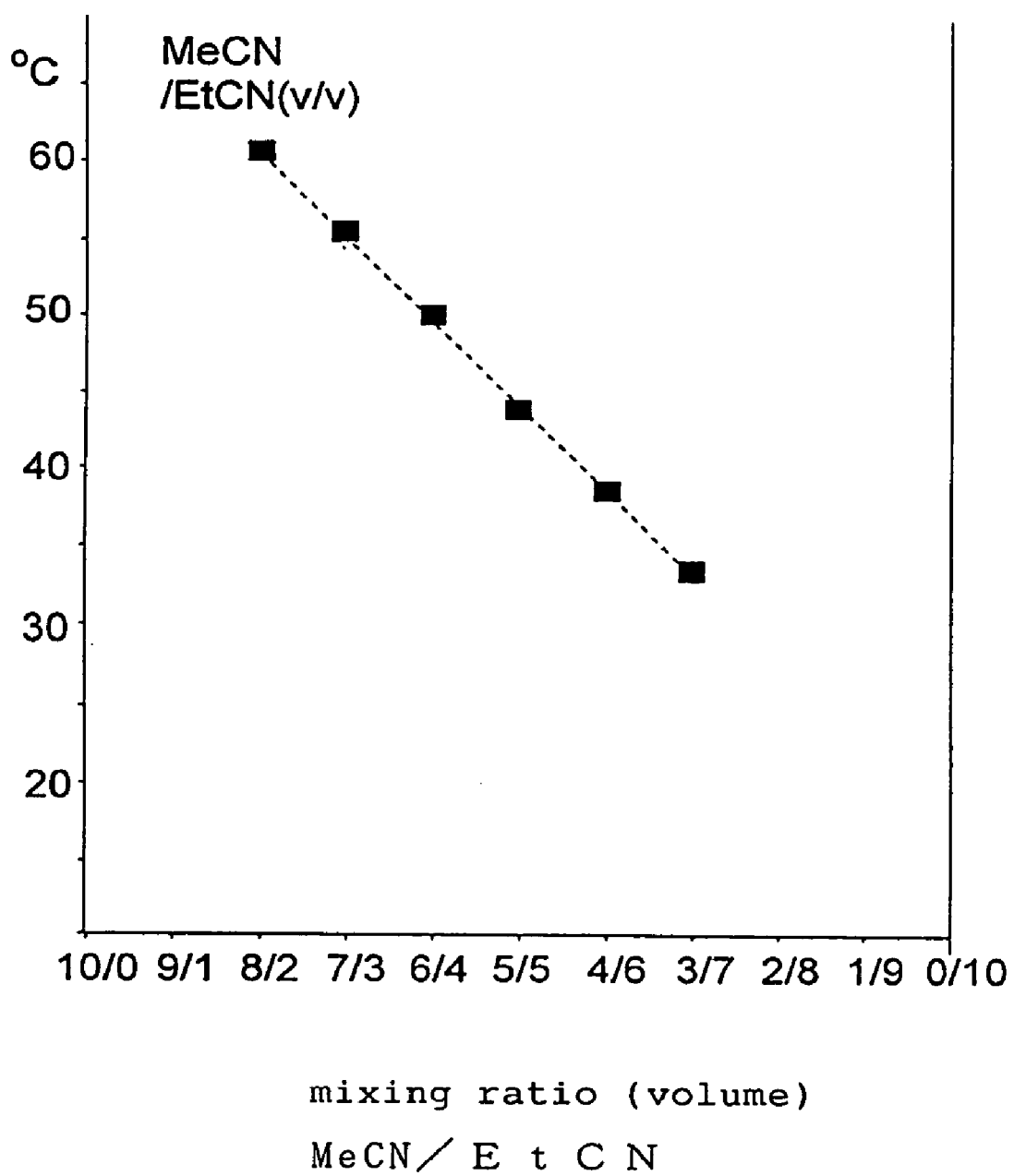
FIG. 4 shows the correlation between mixing ratio, temperature and change of homogeneous compatibilized mixed solvent system—separated solvent system of cyclohexane CH—acetonitrile AN—propionitrile PN mixed solvent system.

The temperature characteristic of the state change of cyclohexane(CH)—acetonitrile(AN)—propionitrile(PN) mixed solvent system to homogeneous compatibilized mixed solvent system. FIG. 4.

Under the condition of 10° C., 1 atmospheric pressure, to 50 mL of cyclohexane contained in a reactive container (glass), 50 mL of mixed solvent of acetonitrile (MeCN) and propionitrile (EtCN) which are nitrile organic solvent was added. As the nitrile organic solvents, the mixture of MeCN and EtCN whose mixing ratio were changed as follows were prepared. 10:0 (50 mL:0 mL), 9:1 (45 mL:5 mL), 8:1 (40 mL:10 mL), 7:3 (35 mL:15 mL), 6:4 (30 mL:20 mL), 5:5 (25 mL:25 mL), 4:6 (20 mL; 30 mL), 3:7 (15 mL:35 mL), 2:8 (10 mL:40 mL), 1:9 (5 mL:45 mL) and 0:10 (0 mL:50 mL). Among these 11 kinds of organic solvent mixture, the mixtures of mixing ratio of MeCN/EtCN is 2:8 or more were separated to 2 phases (upper layer whose main component is cyclohexane and lower layer whose main component is nitrile organic solvent) at 10° C. (separated solvent system). When the temperatures of these solvents were elevated gradually, these solvents became complete homogeneous compatibilized mixed solvents by elevating the temperature over than the temperature shown in the graph. These homogeneous compatibilized mixed solvent systems could maintain the state of homogeneous solution without performing physical operation such as stirring from outside, as long as keeping the temperature higher than the homogenized temperature. And, when the solvents were cooled down lower than the homogenized temperature, these solvents separated to two phases (separated solvent system) immediately. The state change phenomenon of homogeneous compatibilized mixed solvent system—separated solvent system was possible repeatably and reversibly to be performed along with heating or cooling process.

Above mentioned Examples are illustrating that, when the solvent system of the present invention is used, the state of homogeneous compatibilized mixed solvent systems which dissolves chemical component homogeneously is separated to a phase whose main component is single organic solvent composing the solvent system and a phase whose main component is mixed organic solvent, and said chemical component is separated and contained in either one separated phase, in other words, this solvent system is the solvent system which can easily separate the chemical component after chemical reaction.

Illustration of dissolving process of a photo chemical reactive initiator into homogeneous compatibilized mixed solvent system and refining process of the photo chemical reactive initiator to the separated phase of separated solvent system.

Example 5

Under the condition of 25° C. and 1 atmospheric pressure, mixed solvent of cyclohexane:nitroethane:nitromethane 15:4:1 (15 mL:4 mL: 1 mL) was contained into a glass container. Under this temperature condition, the solvent was separated to an upper layer whose main component is cyclohexane and a lower layer whose main component is nitroalkane (mixture of nitromethane and nitroethane). When 1 mg of methylene blue (photo chemical reactive initiator) was added to this solvent system, more than 99.9% of it was dissolved into the lower layer. Then, this mixed solution became homogeneous compatibilized mixed solvent by heating to 45° C., and also methylene blue was dissolved into homogeneous compatibilized mixed solvent. Further, when this solution was cooled down to 25° C., the solution separated to two phases (separated solvent system) immediately and more than 99.9% of methylene blue was dissolved in the lower layer (nitroalkane layer). In the case of nitroalkane mixture (ratio, nitromethane: nitroethane is 4:1) used in the present invention, methylene blue could be refined by changing the ratio of cyclohexane and nitroalkane voluntarily and repeat the state change of homogeneous compatibilized mixed solvent system—separated solvent system and in separated solvent system methylene blue could be refined in nitroalkane phase.

Example 6

In this Example, a selective oxidation reaction using solvent system containing electrolyte and oxidizable organic compound is shown. The state change of homogeneous compatibilized mixed solvent system—separated solvent system and reactivity are shown in FIG. 5.

Under the condition of 25° C. and 1 atmospheric pressure, mixed solvent of cyclohexane:nitroethane:nitromethane 1:3:2 (cyclohexane: nitroethane:nitromethane=1 mL:3 mL:2 mL) was prepared. This organic solvent system was separated to two phases. To this mixed solvent, 200 mg of lithium perchlorate as a supporting electrolyte and 10 mg of hexadecanethiol as an electrolytic substrate were added. To the lower layer of this solution (main component is nitroalkane, and mainly lithium perchlorate is dissolved), a glassy carbon electrode (working electrode), a platinum cathode and silver-silver chloride electrode are inserted and cycled from −0.2 to 2.0 volt (cyclic voltanometory) and potential is changed by 100 mv/second, and corresponding electric current is measured. Since the solvent system was in the state of separated solvent state at this temperature, consequently the oxidation of hexadecanethiol did not occurred, and the remarkable peak showing the oxidation of thiol group was not observed.

After that, when this solution was heated to 55° C., the whole changed to homogeneous solution (homogeneous compatibilized mixed solvent system).

In said state, electric potential-electric current curve was measured, and the signal which indicates remarkably oxidation of thiol group was measured. Further, when cooled down to 20° C. again and electric potential—electric current curve was measured, this oxidation wave did not observed. From above mentioned phenomena, it became clear that in the state of phase separation (separated solvent system) at 20° C., since the most of supporting electrolyte is dissolved in the lower layer (nitroalkane phase) and the most of electrolyte substrate is dissolved in the upper layer (cyclohexane phase), the electron transportation on the surface of electrode does not occur. However, after changed to the homogeneous compatibilized mixed solvent system, since supporting electrolyte and electrolyte substrate are dissolved in homogeneous compatibilized solution, electric discharge to the electrode occurs easily. As mentioned above, by the present invention, it is possible to change the distribution state of electrolyte or solute in the solvent system by controlling small temperature change, and to control the progressing or selectivity of chemical reaction.

Example 7

Electrolysis Diels-Alder reaction of octadecyl2,5-dihydroxybenzoate and 2,3-dimethylbuthadiene.

12 mg of octadecyl2,5-dihydroxybenzoate and 30 mg of 2,3-dimethyl butadiene were dissolved into 5 mL of cyclohexane, further 3 mL of nitroethane, 2 mL of nitromethane and 50 mL of acetic acid were added. Under the condition of 25° C. and 1 atmospheric pressure, this solution was separated to two phases. When this solution was heated to 68° C. (1 atmospheric pressure), it turned to homogeneous solution. In this state, the quantity of electricity corresponding to 2.2 electron per 1 molecule of benzoate was charged by terminal voltage 2.0 volt, electric current 0.3 mA, using glassy carbon plate as an anode and platinum plate as a cathode. After that, the reaction solution was cooled to 25 so as to separate to 2 phases, then the product was refined from the hexane phase. Yield was 48%.

Above reaction is shown in schema1.

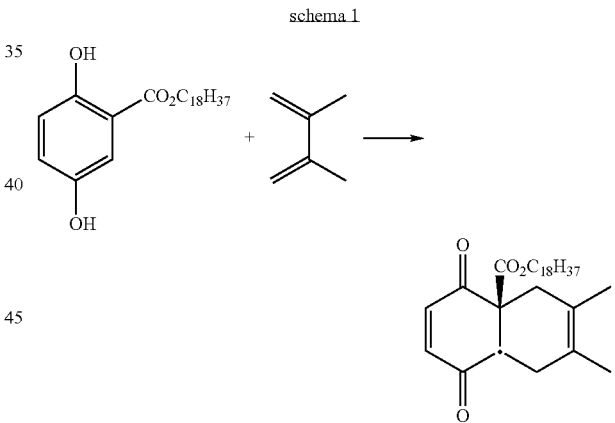

Example 8

Synthesis of Cumarone by Photoelectron Transportation

Under the condition of 25° C. and 1 atmospheric pressure, 5.2 mg of 3-[1-(2-hydroxy-4,6-dimethoxyphenyl)-3-methylbutylthio] propanoic acid and 7.2 mg of α-phellandrene were added to the solvent system consisting of of 5 mL of cyclohexane, 4 mL of nitroethane and 1 mL of nitromethane contained in a pyrex glass container and dissolved. Further, 264 mg of lithium perchloride (acceleration of carbon-sulfur cleavage reaction along with the photo electron transportation of a sulfur atom progressed by light irradiation to methylene blue and acceleration of inner molecular ring forming reaction) and 2.3 mg of methylene blue were added and dissolved completely. Lithium perchloride and methylene blue were completely dissolved in the lower layer (nitroalkane layer).

By heating this solution to 55° C., homogenized completely and under the argon gas flow halogen lamp (visible ray lamp, wave length from 400 nm to 700 nm) was irradiated for 4 hours. After irradiation, by cooling the reaction solution to 25° C., phase separation occurred again (separated solution system). In the lower layer, methylene blue, lithium perchloride, disulfide generated along with the progress of the reaction and un-reacted starting materials were refined. And, in the cyclohexane layer, the reacted product is refined. Yield is 53%.

Above reaction is shown in schema 2.

schema 2

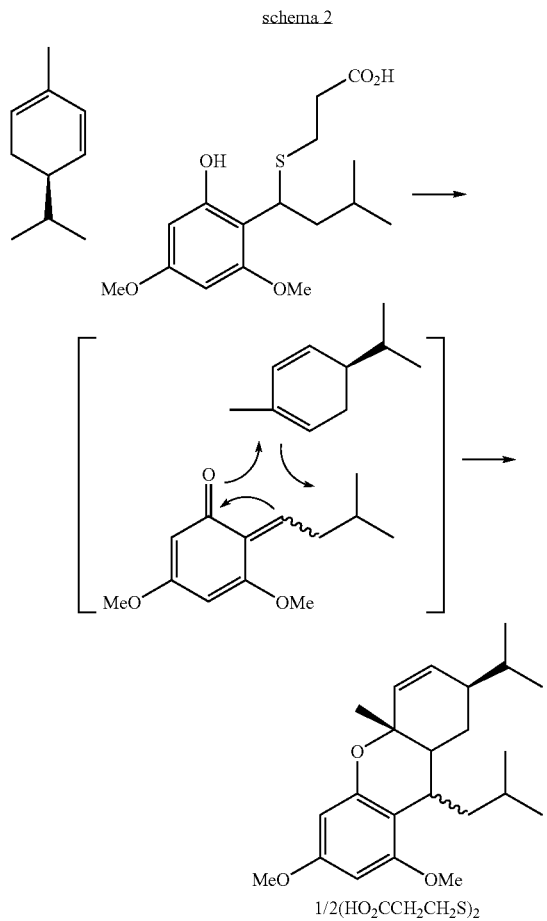

1/2(HO$_2$CCH$_2$CH$_2$S)$_2$

In electrode reaction, supporting electrolyte and organic solvent which dissolves the supporting electrolyte are necessary besides the electrolysis substrate (oxidizable substance, in the case of electrolysis oxidation). In general, electrolysis substrate and supporting salt are added into single compatibilized solution and carry out the electrode reaction and after reaction, the product obtained by chemical transformation from the electrolysis substrate and the supporting salt must be separated. In Examples 5, 6, 7 and 8, by using the solvent system which can perform the state change of two states reversibly, that is, the homogeneous compatibilized mixed solvent system and the separated solvent system, by changing the temperature, the chemical reaction (photo chemical reaction, electrolysis reaction) is carried out in the state of homogeneous compatibilized mixed solvent system and in the state of separated solvent system, the separation of 2 or more components (for example, product and electrolyte) can be realized.

Preparation Examples of Peptide;

Example 9

Liquid phase synthesis of soluble carrier [SC]-Valine (Val)-glycine (Gly)-phenylalanine (Phe)-Fmoc [(SC)-Val-Gly-Phe-Fmoc)]

As the soluble carrier [SC], (3,4,5-trioctadecyloxyphenyl) methane-1-ol, which is R is $C_{18}H_{37}$—, X is 0, n is 3, Q is $CH_2$ and $R_2$ is OH in general formulae B was used.

Process (1) Fmoc-Val (170 mg) was dissolved in 3 mL of dichloromethane, and 125 mg of dicyclohexylcarbodiimide (DCC) was added. This solution was stirred for 15 minutes at the room temperature, then filtrated. After the filtrate was concentrated and solidified using a rotary evaporator, the obtained residue was dissolved in 3 mL of dimethylformamide (DMF). Then 3 mL of cyclohexane solution in which soluble carrier [SC] is dissolved (soluble carrier 50 mg/3 mL) was added to the DMF solution. Further, 6.5 mg of 4-dimethylaminopyridine (DMAP) was added, the reaction solution was heated to 50° C. and reacted for 30 minutes. The solution separated to the cyclohexane layer and the DMF layer changed to homogeneous solvent. After the reaction, the reaction solution was cooled down to the room temperature and made the reaction solution separate to two phases. The DMF phase of the lower layer was separated and removed, then 3 mL of 10% diethylamine/DMF solution was added and stirred for 20 minutes at 50° C. The reaction solution was cooled and the cyclohexane layer was separated. In this cyclohexane layer, soluble carrier bonded Valine-NH$_2$([SC]-Val-NH$_2$) was refined (yield was 95%).

Process (2) 57 mg of Fmoc-Gly, 55 mg of HOBt and 25 mg of diisopropylcarbodiimide (DIPCD) were dissolved in 2 mL of DMF and stirred for 150 minutes at the room temperature. This solution was used as the activated Fmoc-Gly-OH/DMF solution. That is, after 2 mL of this solution was cooled down to 5, 2 mL of [SC]-Val-NH$_2$/cyclohexane obtained in Process (1) was added. The temperature of the reaction solution was elevated from 5° C. to 50° C. by 1 hour and maintain at 50° C. for 30 minutes. Finally, when the reaction solution was cooled down to the room temperature, the reaction solution separated to two layers, and from the upper layer (cyclohexane layer) the aimed product [SC]-Val-Gly-Fmoc) (process A in extending process) was separated. Fmoc group was removed by adding diethylamine and [SC]-Val-Gly-NH$_2$ (process B in extending process) was obtained.

The outline of this synthesis reaction is same as shown in afore mentioned extending process.

Process (3) Then, 57 mg of Fmoc-Phe, 55 mg of HOBt and 25 mg of diisopropylcarbodiimide (DIPCD) were dissolved in 2 mL of DMF and stirred for 150 minutes at the room temperature. This solution was used as the activated Fmoc-phenylalanyl(Phe)-OH/DMF solution. That is, after cooled 2 ml of this solution to 5, 2 mL of [SC]-Val-Gly-NH$_2$/cyclohexane solution obtained in process (2) was added. The temperature of the reaction solution was elevated from 5° C. to 50° C. by 1 hour and maintain at 50° C. for 30 minutes. Finally, when the reaction solution was cooled down to the room temperature, the reaction solution separated to two layers, and from the upper layer (cyclohexane layer) the aimed product [SC]-Val-Gly-Phe-Fmoc) (process A in extending process) was separated.

By repeating above mentioned operation, amino acids are bonded to soluble carrier gradually and aimed oligo peptide was synthesized.

Confirmation of the Structure

[SC] cyclohexame soluble carrier;
(3,4,5-trioctadecyloxyphenyl)methane-1-ol $^1$H-NMR (400 MHz) δ; 5.54 (2H, s), 4.58 (2H, d, J=5.1 Hz), 3.96 (4H, t, J=6.6 Hz), 3.96 (3H, s), 1.82-1.70 (6H, m), 1.50-1.41 (6H, m), 1.38-1.20 (84H, br), 0.88 (9H, 6, 8 Hz); $^{13}$C-NMR (100 Hz); (100 MHz δ: 153-2, 137.4, 136.0, 105.2, 73.4, 69.1, 65.7, 32.0, 30.4, 29.8, 29.7, 29.5, 26.2, 22.8, 14.2; MALDI TOF-MS (pos), to $C_{61}H_{116}O_4$ [M+Na]$^+$, calculated value is 935, experimental value is 935.

[SC]-Val-Fmoc $^1$H-NMR (CDCl$_3$) δ 7.76 (2H, d, J=7.7 Hz), 7.60 (2H, d, J=7.7 Hz), 7.40 (2H, dt, J=2.6, 7.3 Hz), 7.31 (22H, t, J=7.3 Hz), 6.53 (2H, s), 5.31 (1H, d, J=9.2 Hz), 5.11 (1H, d, J=12.1 Hz), 5.05 (1H, d, J=12.1 Hz), 4.38 (2H, m), 4.23 (1H, t, J=7.3 Hz), 3.94 (6H, m), 2.19 (1H, m), 1.78 (4H, m), 1.73 (2H, m), 1.45 (6H, m), 1.35-1.23 (84H, br.), 0.95 (3H, d, J=7.0 Hz), 0.88 (12H, m); $^{13}$C-NMR (CDCl$_3$) δ 172.0, 156.2, 153.2, 143.9, 143.8, 141.3, 138.4, 130.2, 128, 3, 127.7, 127.1, 125.1, 120.0, 107.1, 73.4, 69.2, 67.4, 67.1, 59.0, 47.2, 32.0, 31.4, 30.3, 29.8, 29.7, 29.5, 29.4, 26.1, 22.7, 14.1;TOF-MS (pos) MF, to $C_{81}H_{135}NO_7$ [M+Na]$^+$, calculated value is 1257, experimental value is 1257.

[SC]-Val-NH$_2$; $^1$H-NMR (400 MHz) δ: 6.54 (2H, s), 5.07 (1H, d, J=12.1 Hz), 503 (1H, d, J=12.1 Hz), 3.95 (4H, t, J=6.6 Hz), 3.94 (2H, t, J=6.6 Hz), 3.33 (2H, d, J=5.1 Hz), 2.07-2.01 (1H, m), 1.81-1.77 (4H, m), 1.76-1.71 (2H, m), 1.49-1.43 (6H, m), 1.37-1.23 (84H, br), 0.96 (3H, d, J=7.0 Hz), 0.89-0.86 (12H, m); $^{13}$C-NMR (150 MHz) δ, 175.4, 153.2, 138.3, 130.7, 107.1, 73.4, 69.2, 66.8, 59.9, 32.2, 32.0, 30.3, 29.8, 29.7, 29.6, 29.4, 26.1, 22.7, 19.3, 17.1, 14.1; TOF-MS (pos), to $C_{66}H_{125}NO_5$ [M+Na]$^+$, calculated value is 1034, experimental value is 1034.

[SC]-Val-Gly-Fmoc $^1$H-NMR (400 MHz) δ:7.77 (2H, d, J=7.3 Hz), 7.59 (2H, d, J=7.3 Hz), 7.40 (2H, t, J=7.3 Hz), 7.31 (2H, dt, J=0.7, 7.3 Hz), 6.52 (2H, s), 6.38 (1H, d, J=8.4 Hz), 5.44-5.37 (1H, br), 5.10 (1H, d, J=12.1 Hz), 5.02 (1H, d, J=12.1 Hz), 4.62 (2H, dd, J=8.4, 4.8 Hz), 4.42 (2H, d, J=7.0 Hz), 4.24 (1H, t, J=7.0 Hz), 3.96-3.92 (8H, m), 2.21-2.16 (1H, m), 1.81-1.76 (4H, m), 1.75-1.70 (2H, m), 1.48-1.43 (66H, m), 1.37-1.21 (84H, br), 0.91 (3H, d, J=7.0 Hz), 0.88 (9H, t, J=7.0 Hz), 0.86 (3H, d, J=7.0 Hz); $^{13}$C-NMR (150 MHz) 5:171.5, 168.7, 156.5, 153.1, 143.6, 141.2, 138.3, 130.0, 127.7, 127.0, 125.0, 120.0, 107.0, 73.4, 69.2, 67.5, 67.4, 57.1, 47.1, 32.0, 31.4, 30.4, 29.8, 29.7, 29.5, 29.4, 26.1, 22.8, 19.0, 17.7, 14.2; MALDI TOF-MS (pos) to $C_{83}H_{138}N_2O_8$ [M+Na]$^+$, calculated value is 1314, experimental value is 1314.

[SC]-Val-Gly-NH$_2$ $^1$H-NMR (600 MHz) δ:7.74 (1H, d, J=9.2 Hz), 6.53 (2H, s), 5.11 (1H, d, J=12.1 Hz), 5.02 (1H, d, J=12.1 Hz), 4.61 (1H, dd, J=9.2, 5.1 Hz), 3.95 (4H, t, J=6.6 Hz), 3.94 (2H, t, J=6.6 Hz), 3.39 (2H, s), 2.24-2.18 (1H, m), 1.81-1.76 (4H, m), 1.75-1.71 (2H, m), 1.49-1.44 (6H, m), 1.37-1.20 (84H, br), 0.93 (3H, d, J=7.0 Hz), 0.90-0.86 (12H, m); $^{13}$C-NMR (150 MHz) δ:172.6, 171.8, 153.1, 130.3, 125.5, 106.9, 73.4, 69.2, 67.2, 56.6, 44.8, 32.0, 31.3, 30.4, 30.3, 29.8, 29.7, 29.5, 29.4, 26.2, 22.8, 19.1, 17.8, 14.2;MALDI TOF-MS (pos), to $C_{68}H_{128}N_2O_6$ [M+Na]$^+$, calculated value is 1091, experimental value is 1091.

[SC]-Val-Gly-Phe-Fmoc $^1$H-NMR (600 MHz) δ:7.75 (2H, d, J=7.7 Hz), 7.53-7.49 (2H, m), 7.39 (2H, dd, J=7.3, 2.2 Hz), 7.30-7.27 (4H, m), 7.25-7.21 (1H, m), 7.20-7.15 (2H, br), 6.76-6.69 (1H, br), 6.60-6.55 (1H, br), 6.50 (2H, s), 5.40-5.34 (1H, br), 5.07 (1H, d, J=12.1 Hz), 4.99 (1H, d, J=12.1 Hz), 4.56 (1H, dd, J=8.8, 4.8 Hz), 4.46-4.30 (2H, m), 4.17 (1H, t, J=7.0 Hz), 4.10-4.03 (1H, m), 3.92 (6H, t, J=6.6 Hz), 3.83-3.76 (2H, m), 3.18-3.11 (1H, m), 3.10-3.02 (1H, m), 2.20-2.13 (1H, m), 1.79-1.69 (6H, m), 1.48-1.41 (6H, m), 1.35-1.23 (84H, br.m), 0.91-0.85 (15H, m); $^{13}$C-NMR (150 MHz) δ:171.5, 171.3, 168.3, 156.0, 153, 1, 143.6, 141.2, 138.2, 136.2, 130.1, 129.1, 128.8, 127.7, 127.1, 127.0, 125.0, 124.9, 120.0, 107.0, 73.4, 69.2, 67.5, 67.1, 57.3, 47.2, 32.0, 31.3, 30.4, 29.8, 29.7, 29.5, 29.4, 26.2, 22.8, 19.0, 17.8, 14.2; MALDI TOF-MS (pos), to $C_{92}H_{147}N_3O_9$ [M+Na]$^+$, calculated value is 1461, experimental value is 1461.

[SC]-Val-Gly-Phe-NH$_2$ $^1$H-NMR (400 MHz) δ:7.99-7.93 (1H, m), 7.35-7.30 (2H, m), 7.27-7.21 (3H, m), 6.66 (1H, d, J=8.8 Hz), 6.52 (2H, s), 5.11 (1H, d, J=12.1), 5.02 (1H, d, J=12.1 Hz), 4.58 (1H, dd, J=8.8, 4.8 Hz), 4.05 (1H, d, J=5.9 Hz, minor), 4.01 (1H, d, J=5.9 Hz, major), 3.98-3.91 (7H, m), 3.66 (1H, d, J=10.0 Hz), 3.32 (1H, dd, J=13.6, 3.9 Hz), 2.67 (1H, dd, J=13.6, 10.0 Hz), 2.24-2.15 (1H, m), 1.82-1.69 (6H, m), 1.50-1.39 (6H, m), 1.37-1.21 (84H, br), 0.92 (3H, d, J=6.8 Hz), 0.90-0.85 (12H, m); $^{13}$C-NMR (150 MHz) δ:175.2, 171.5, 168.9, 153.1, 151.4, 137.7, 129.2, 128.8, 126.9, 125.5, 107.0, 73.5, 69.2, 67.5, 57.2, 56.5, 43.4, 40.9, 32.0, 31.3, 30.4, 29.8, 29.7, 29.5, 29.4, 26.2, 22.8, 19.1, 17.7, 14.2; MALDI TOF-MS (pos), to $C_{77}H_{137}N_3O_7$ [M+Na]$^+$, calculated value is 1239, experimental value is 1239.

Example 10

Liquid-phase synthesis of [SC]-Val-Phe-Fmoc 63 mg of Fmoc-Phe, 63 mg of HOBt and 25 mg of diisopropylcarbodiimide (DIPCD) were dissolved in 2 mL of DMF and stirred for 150 minutes at the room temperature. This solution was used as the activated Fmoc-Phe/DMF solution. That is, after 2 mL of this solution was cooled to 5° C., [SC]-Val-NH$_2$/cyclohexane solution (2 mL) obtained in process 1 of Example 1 was added. The temperature of the reaction solution was elevated from 5° C. to 50° C. slowly by one hour, further maintained at 50° C. for 30 minutes. As the final, when the reaction solution was cooled down to the room temperature, the solution was separated to two layers again. From the upper layer (cyclohexane layer), the aimed product [SC]-Val-Phe-Fmoc was separated.

By repeating above operations, amino acids were bonded to the soluble carrier consecutively and the aimed peptide was synthesized.

Example 11

Liquid phase synthesis of [SC]-Val-Pro-Fmoc 53 mg of Fmoc-Pro, 57 mg of HOBt and 25 mg of diisopropylcarbodiimide (DIPCD) were dissolved in 2 mL of DMF and stirred for 150 minutes at the room temperature. This solution was used as the activated Fmoc-Pro-OH/DMF solution. That is, after 2 mL of this solution was cooled to 5° C., [SC]-Val-NH$_2$/cyclohexane solution (2 mL) obtained in process 1 of Example 1 was added. The temperature of the reaction solution was elevated from 5° C. to 50° C. slowly by one hour, further maintained at 50° C. for 30 minutes. As the final, when the reaction solution was cooled down to the room temperature, the solution was separated to two layers again. From the upper layer (cyclohexane layer), the aimed product [SC]-Val-Pro-Fmoc was separated.

By repeating above operations, amino acids were bonded to the soluble carrier consecutively and the aimed peptide was synthesized.

Example 12

Liquid phase synthesis of [SC]-Val-Ala-Fmoc 50 mg of Fmoc-Ala, 53 mg of HOBt and 25 mg of diisopropylcarbodiimide (DIPCD) were dissolved in 2 mL of DMF and stirred for 150 minutes at the room temperature. This solution was used as the activated Fmoc-Ala-OH/DMF solution. That is, after 2 mL of this solution was cooled to 5° C., [SC]-Val-NH$_2$/cyclohexane solution (2 mL) obtained in process 1 of Example 1 was added. The temperature of the reaction solution was elevated from 5° C. to 50° C. slowly by one hour, further maintained at 50° C. for 30 minutes. As the final, when the reaction solution was cooled down to the room temperature, the solution was separated to two layers again. From the upper layer (cyclohexane layer), the aimed product [SC]-Val-Ala-Fmoc was separated.

By repeating above operations, amino acids were bonded to the soluble carrier consecutively and the aimed peptide was synthesized.

INDUSTRIAL APPLICABILITY

As mentioned above, by using the solvent system of the present invention, the state change of the homogeneous compatibilized mixed solvent system and the separated solvent system can easily control by changing temperature, and by the controlling of the state change, the excellent effect that can perform the treating system or reacting system handling the chemical substances in which the controlling of reaction and the separation-refining of the product can be easily realised is provided. Further, since by the state change of the homogeneous compatibilized mixed solvent system and the separated solvent system the electric characteristics can be controlled, it is possible to design the functional system utilizing these characteristics, and the excellent effect to expect to perform a novel technique is provided.

Still more, in the synthesis of peptide utilizing said solvent system, following excellent effect is provided by the present invention. That is, a method for liquid phase synthesis of peptide which can be more easily controlled and more easily refine the product compared with the method for solid phase peptide synthesis is provided, by designing a carrier which makes soluble the compound to which amino acid residue of carboxy end of peptide to be synthesized and the compound to which peptide is bonded in one solvent consisting the reaction solvent system, and by combining said carrier with said solvent system.

What is claim:

1. A method for preparation of a peptide by liquid phase synthesis, comprising
providing a solvent system, the solvent system comprising a first solvent or mixed solvent A and a second solvent or mixed solvent B, wherein the solvent system can change phase states reversibly in response to a change in temperature between a first phase state, which is a homogenously compatibilized mixed solvent system in which the first solvent or mixed solvent A and the second solvent or mixed solvent B are homogenously compatibilized and mixed, and a second phase state, in which the first solvent or mixed solvent A is present in a separate phase from the second solvent or mixed solvent B such that the solvent system is separated into two or more phases,
combining the solvent system with a compound comprising a carrier, the compound having solubility in the first solvent or mixed solvent A of the solvent system,
dissolving a compound comprising one or more amino acids in the first solvent or mixed solvent A, in the second solvent or mixed solvent B, or in said solvent system in the first phase state,
forming said solvent system in the first phase state that is homogenously compatibilized by placing the solvent system at a first temperature,
extending said compound comprising one or more amino acids by introducing an amino acid to the carboxy end of said compound to form a peptide product, wherein the solvent system is preferentially at a second temperature lower than the first temperature and wherein the solvent system at the second temperature remains in the first phase state that is homogenously compatibilized,
changing the temperature condition so that the solvent system transitions from the first phase state to the second phase state, in which the first solvent or mixed solvent A is present in a separate phase from the second solvent or mixed solvent B, and
recovering the peptide product from one of the separate phases.

2. The method for preparation of a peptide by liquid phase synthesis of claim 1, wherein the carrier consists of an aromatic ring moiety and alkyl chains having 10 or more carbons as a fundamental skeleton represented by general formula A which has a functional group for bonding an amino acid with a cycloalkanephilic moiety at the end,

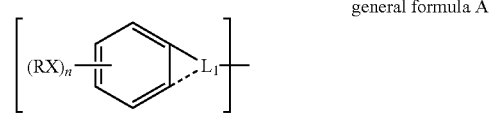

general formula A wherein $L_1$ is a hydroxyl group which bonds with amino acid, a single bond which bonds with a thiol group, an amino group or a carbonyl group, a group which bonds with said hydroxyl group, a thiol group, an amino group or a carbonyl group or an atomic a group which forms fused aromatic ring of two rings bonded with the dotted line of general formula A, wherein the dotted line is a group which forms said fused aromatic ring by bonding with H or $L_1$, X is an O, an N, an S an ester group, a sulfide group or an imino group, R is a hydro carbon group with 10 or more carbon atoms which can contain O, S or N having a possibility to improve the solubility of the carrier in cycloalkane solvents as a bonding atom, n is an integer from 1 to 5, further in the case when said hydro carbon group with 10 or more carbon atoms is to improve the solubility of the carrier in cycloalkane solvents, R possesses a side chain with a functional group which bonds with the amino group and/or substituent.

3. The method for preparation of a peptide by liquid phase synthesis of claim 2, wherein the compound represented by general formula A is a compound selected from the group represented by general formulae B

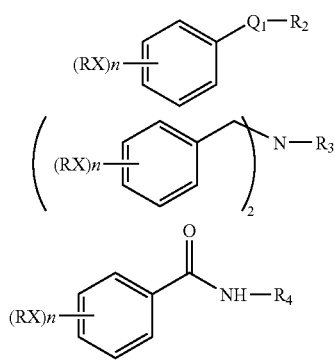

general formulae B wherein, X, R and n are the same as to that of general formula A, Q is a single bond or hydro carbon group, $R_2$ is a hydroxyl group, a thiol group, an amino group or a carbonyl group which bonds with amino acid, and $R_3$ and $R_4$ are groups represented by general formula C,

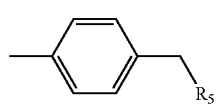

general formula C wherein, $R_5$ is a hydroxyl group, a thiol group, an amino group or a carbonyl group which bonds with amino acid.

4. The method for preparation of a peptide by liquid phase synthesis of claim 1, wherein the first solvent or mixed solvent A comprises a cycloalkane, and the second solvent or mixed solvent B comprises at least one selected from the group consisting of a nitroalkane, a nitrile, an alcohol, a halogenated alkyl, an amide and a sulfoxide.

5. The method for preparation of a peptide by liquid phase synthesis of claim 4, wherein the carrier consists of an aromatic ring moiety and alkyl chains having 10 or more carbons as a fundamental skeleton represented by general formula A which has a functional group for bonding an amino acid with the cycloalkanephilic moiety at the end.

6. The method for preparation of a peptide by liquid phase synthesis of claim 5, wherein the compound represented by general formula A is the compound selected from the general formulae B.

7. The method for preparation of a peptide by liquid phase synthesis of claim 4, wherein an alkyl group of nitro alkane has 1, 2 or 3 carbon atoms, an alkyl group of nitrile has 1, 2 or 3 carbon atoms, the amide is N-dialkyl or N-monoalkyl amide, the alkyl group and formyl group or acyl group have 6 or less carbon atoms, the alcohol has 8 or less carbon atoms, an alkyl group of sulfoxide has 1, 2 or 3 carbon atoms and an alkyl group of halogenated alkyl has 6 or less carbon atoms.

8. The method for preparation of a peptide by liquid phase synthesis of claim 7, wherein the carrier consists of an aromatic ring moiety and alkyl chains having 10 or more carbons as a fundamental skeleton represented by general formula A which has a functional group for bonding an amino acid with a cycloalkanephilic moiety at the end.

9. The method for preparation of a peptide by liquid phase synthesis of claim 8, wherein the compound represented by general formula A is the compound selected from the group of represented by general formulae B.

10. The method for preparation of a peptide by liquid phase synthesis of claim 1, further comprising the step of substituting the second solvent or mixed solvent B, which dissolves α-amino protected amino acid, with a solvent C capable of dissolving the peptide product in a phase separated condition, and changing the temperature condition to a temperature where the solvent system changes phase state from said phase separated state to a homogeneous state by heating after substituting the second solvent or mixed solvent B.

11. The method for preparation of a peptide by liquid phase synthesis of claim 1, wherein the first solvent or mixed solvent A comprises cyclohexane and the second solvent system or mixed solvent B comprises one or more selected from the group consisting of nitromethane, nitroethane, acetonitrile, propionitrile, dimethylformamide, and dimethylacetoamide.

* * * * *